(12) United States Patent
Mailoa et al.

(10) Patent No.: US 11,455,439 B2
(45) Date of Patent: Sep. 27, 2022

(54) NEURAL NETWORK FORCE FIELD COMPUTATIONAL ALGORITHMS FOR MOLECULAR DYNAMICS COMPUTER SIMULATIONS

(71) Applicant: Robert Bosch GmbH, Stuttgart (DE)

(72) Inventors: Jonathan Mailoa, Cambridge, MA (US); Mordechai Kornbluth, Brighton, MA (US); Georgy Samsonidze, San Francisco, CA (US); Boris Kozinsky, Waban, MA (US); Nathan Craig, Santa Clara, CA (US)

(73) Assignee: Robert Bosch GmbH, Stuttgart (DE)

( * ) Notice: Subject to any disclaimer, the term of this patent is extended or adjusted under 35 U.S.C. 154(b) by 974 days.

(21) Appl. No.: 16/202,890

(22) Filed: Nov. 28, 2018

(65) Prior Publication Data
US 2020/0167439 A1    May 28, 2020

(51) Int. Cl.
*G06F 30/20*    (2020.01)
*G06N 3/04*    (2006.01)
*G06N 10/00*    (2022.01)

(52) U.S. Cl.
CPC ........... *G06F 30/20* (2020.01); *G06N 3/0454* (2013.01); *G06N 10/00* (2019.01)

(58) Field of Classification Search
CPC .......... G06F 30/20; G06F 30/00; G06F 30/25; G06F 30/27; G06F 2111/10; G06N 3/0454; G06N 10/00; G06N 3/08; G16C 20/70; G16C 10/00; G16C 60/00
USPC .......................................................... 703/6
See application file for complete search history.

(56) References Cited

U.S. PATENT DOCUMENTS 8,843,509 B2    9/2014 Csanyi et al.

OTHER PUBLICATIONS

Behler, Jorg et al., "Generalized Neural-Network Representation of High-Dimensional Potential-Energy Surfaces", Apr. 2, 2007, Physical Review Letters. (Year: 2007).*
Behler, Jorg, "Atom-Centered Symmetry Functions for Constructing High-Dimensional Neural Network Potentials", Feb. 16, 2011, The Journal of Chemical Physics, 134. (Year: 2011).*
Li, Hao et al., "Application of Artificial Neural Networks for Catalysis: A Review", Oct. 18, 2017, MDPI. (Year: 2017).*
Artrith, Nonguch et al., "High Dimensional Neural Network Potentials for Metal Surfaces: A Prototype Study for Copper", Jan. 24, 2012, Physical Review B 85. (Year: 2012).*
Behler, Jörg et al., Neural Network Potential-Energy Surfaces for Atomistic Simulations, The Royal Society of Chemistry, Oct. 5, 2010, DOI: 10.1039/9781849730884-00001, vol. 7, pp. 1-43, Bochum, Germany.

(Continued)

*Primary Examiner* — Cedric Johnson
(74) *Attorney, Agent, or Firm* — Brooks Kushman P.C.

(57) ABSTRACT

A computational method for simulating the motion of elements within a multi-element system using a neural network force field (NNFF). The method includes receiving a combination of a number of rotationally-invariant features and a number of rotationally-covariant features of a local environment of the multi-element system; and predicting a force vector for each element within the multi-element system based on the combination of the number of rotationally-invariant features, the number of rotationally-covariant features, and the NNFF, to obtain a simulated motion of the elements within the multi-element system.

20 Claims, 6 Drawing Sheets

(56) References Cited

OTHER PUBLICATIONS

Jindal, Shweta et al., A Transferable Artificial Neural Network Model for Atomic Forces in Nanoparticles, The Journal of Chemical Physics,, Nov. 16, 2018, pp. 1-29, India.

Huan, Tran Doan et al., A Universal Strategy for the Creation of Machine Learning-Based Atomistic Force Fields, NPJ Computational Materials, Sep. 18, 2017, pp. 1-8, vol. 37, Connecticut.

Barch, Brian et al., Solving Minimum Energy Structures with Neural Networks, Berkley EECS, May 12, 2017, pp. 1-14, Berkley, California.

Behler, Jörg, Atom-Centered Symmetry Functions for Constructingh High-Dimensional Neural Network Potentials, The Journal of Chemical Physics, Feb. 16, 2011, pp. 1-14, vol. 134, 074106, DOI: 10.1063/1.3553717, Bochum, Germany.

Botu, V. et al., Learning Scheme to Predict Atomic Forces and Accelerate Materials Simulations, Physical Review, vol. B 92, 094306, Sep. 25, 2015, pp. 1-5, Connecticut.

Gastegger, Michael et al., Machine Learning Molecular Dynamics for the Simulation of Infrared Spectra, Chem. Sci., May 19, 2017, pp. 1-12, vol. 8, 6924, DOI: 10.1039/c7sc02267k, Vienna, Austria.

Gastegger, Michael, et al., High-Dimensional Neural Network Potentials for Organic Reactions and an Improved Training Algorithm, Journal of Chemical Theory and Computation, Apr. 16, 2015, pp. 2187-2198, vol. 11, DOI: 10.1021/acs.jctc.5b00211, Vienna, Austria.

Li, Wenwen et al., Study of Li Atom Diffusion in Amorphous Li3P04 with Neural Network Potential, The Journal of Chemical Physics, Dec. 5, 2017, pp. 1-11, vol. 147, 214106, DOI: 10.1063/1.4997242, Japan.

Behler, Jörg et al., Generalized Neural-Network Representation of High-Dimensional Potential-Energy Surfaces, The American Physical Society, Physical Review Letters, Apr. 6, 2007, pp. 1-4. PRL 98, 146401, ,Switzerland.

\* cited by examiner

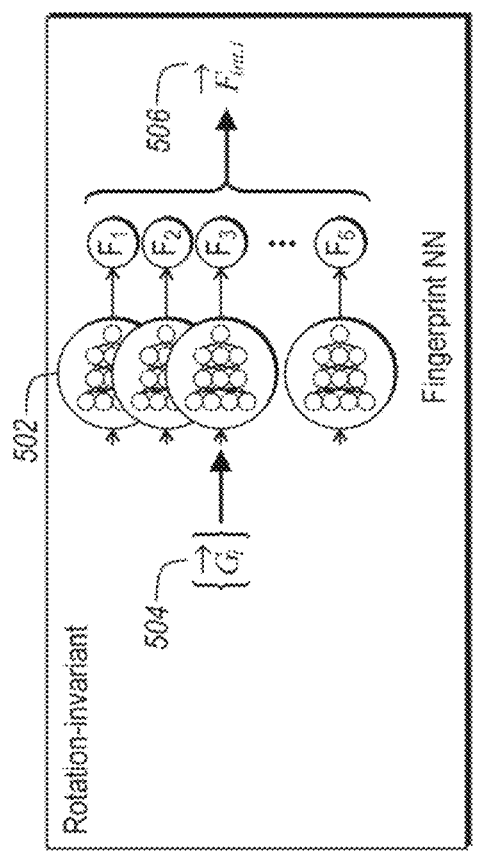
FIG. 5A
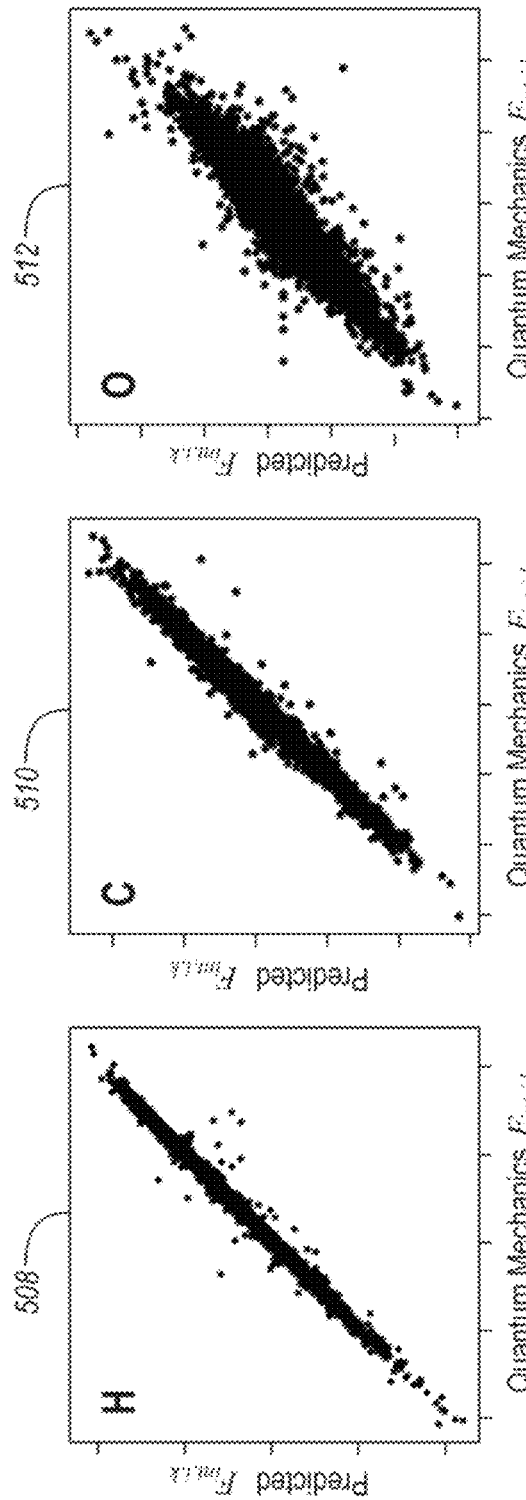
FIG. 5B
FIG. 5C
FIG. 5D

NEURAL NETWORK FORCE FIELD COMPUTATIONAL ALGORITHMS FOR MOLECULAR DYNAMICS COMPUTER SIMULATIONS

CROSS-REFERENCE TO RELATED APPLICATIONS

Technical Field

This invention relates generally to neural network force field (NNFF) computational algorithms for direct prediction of atomic forces in molecular dynamics computer simulations in material systems, such as electrochemical and water filtration devices.

Background

Molecular dynamics is a computational materials science methodology for simulating the motion of atoms in a material system at real operating pressure and temperature conditions. Methodologies exist to calculate the underlying atomic forces used in the simulation of the motion of atoms. One methodology is the ab-initio quantum mechanics approach. This approach is very accurate but is also very expensive because of the tremendous amount of computational resources necessary to apply the approach. While other approaches exist that consume less computational resources, these other approaches do not deliver as much accuracy.

SUMMARY

In a first embodiment, a computational method for simulating the motion of elements within a multi-element system using a neural network force field (NNFF) is disclosed. The method includes receiving a combination of a number of rotationally-invariant features and a number of rotationally-covariant features of a local environment of the multi-element system. The method further includes predicting a force vector for each element within the multi-element system based on the combination of the number of rotationally-invariant features, the number of rotationally-covariant features, and the NNFF, to obtain a simulated motion of the elements within the multi-element system.

In a second embodiment, a non-transitory computer-readable medium tangibly embodying computer readable instructions for a software program is disclosed. The software program is executable by a processor of a computing device to provide operations. The operations include receiving a combination of a number of rotationally-invariant features and a number of rotationally-covariant features of a local environment of the multi-element system. The operations further include predicting a force vector for each element within the multi-element system based on the combination of the number of rotationally-invariant features and the number of rotationally-covariant features, and an NNFF, to obtain a simulated motion of the elements within the multi-element system.

In a third embodiment, a computer system for simulating the motion of elements within a multi-element system using an NNFF is disclosed. The computer system includes a simulation computer having a processor for executing computer-readable instructions and a memory for maintaining the computer-executable instructions. The computer-executable instructions when executed by the processor perform the following functions: receiving a combination of a number of rotationally-invariant features and a number of rotationally-covariant features of a local environment of the multi-element system; and predicting a force vector for each element within the multi-element system based on the combination of the number of rotationally-invariant features and the number of rotationally-covariant features, and the NNFF, to obtain a simulated motion of the elements within the multi-element system.

BRIEF DESCRIPTION OF THE DRAWINGS

FIG. 5A shows a diagram of a fingerprint neural network (NN) of an NNFF algorithm of one embodiment.

FIGS. 5B, 5C, and 5D depict graphs showing results for the prediction of H, C, and O atoms, respectively, of bulk PEO using the fingerprint NN of the NNFF algorithm of one embodiment.

FIG. 7 is a schematic diagram of a computing platform that may be utilized to implement the NNFF algorithms in one or more embodiment, for instance, the NNFF algorithm of FIG. 6a.

DETAILED DESCRIPTION

Figure 1:
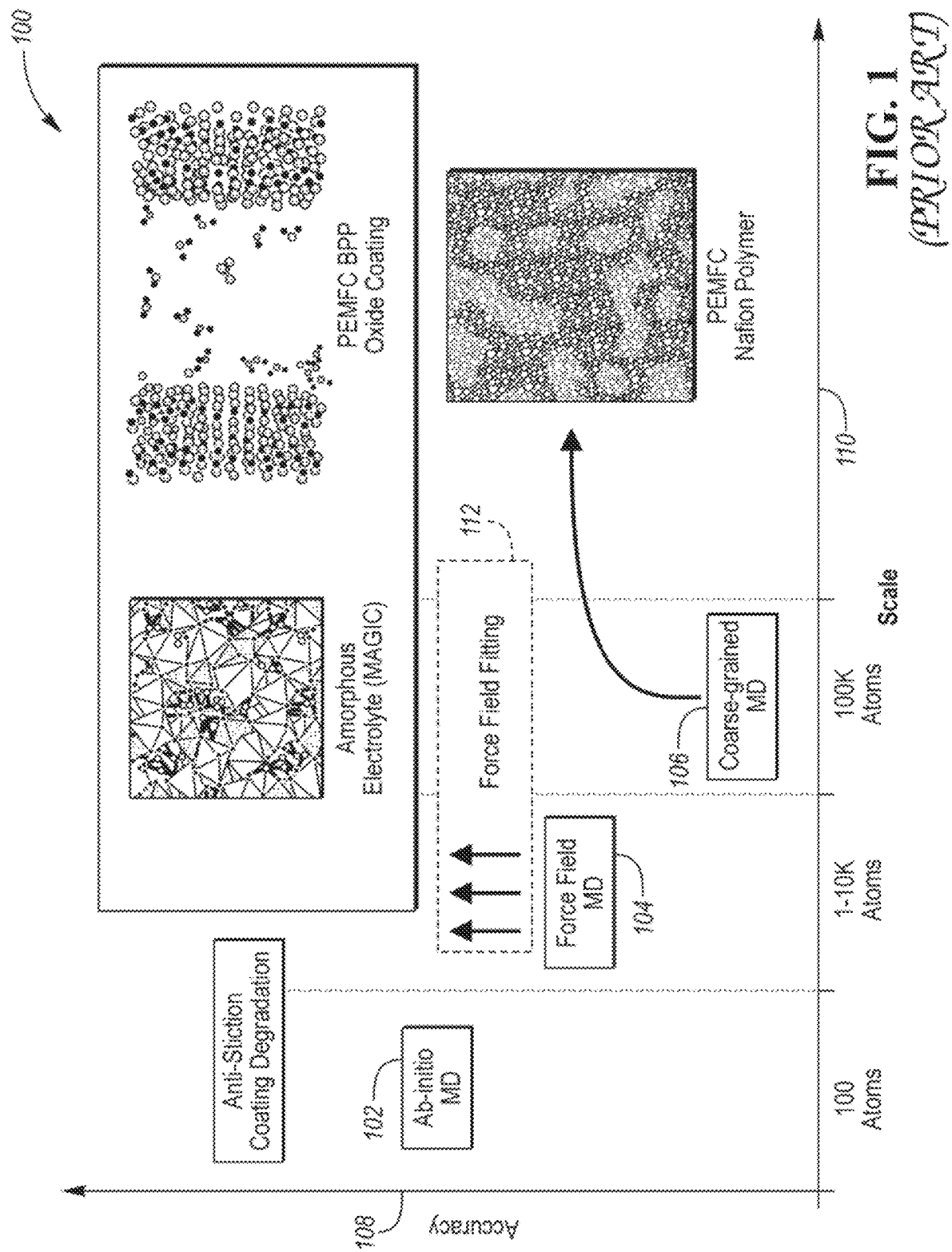
FIG. 1 depicts a schematic graph showing the tradeoff between scale and accuracy for different prior art molecular dynamics (MD) force calculation methods.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

The term "substantially" may be used herein to describe disclosed or claimed embodiments. The term "substantially" may modify a value or relative characteristic disclosed or claimed in the present disclosure. In such instances, "substantially" may signify that the value or relative characteristic it modifies is within ±0%, 0.1%, 0.5%, 1%, 2%, 3%, 4%, 5% or 10% of the value or relative characteristic.

Molecular dynamics (MDs) methodologies are beneficial for studying physical phenomena, such as, but not limited to, ionic transport, chemical reactions, and material bulk and surface degradation in material systems, such as devices or functional materials. Non-limiting examples of such material systems include fuel cells, surface coatings, batteries, water desalination, and water filtration. Methodologies exist to calculate the underlying atomic forces used in the simulation of the motion of atoms. The ab-initio quantum mechanics approach is very accurate but is also very expensive because of the tremendous amount of computational resources necessary to apply the approach.

Neural networks have been utilized to fit and predict quantum mechanics energies. These methodologies have been referred to as neural network force fields (NNFF). Derivatives of energy with respect to atomic positions and forces are predicted using quantum mechanics energies. However, these methodologies are also computationally extensive. In light of the foregoing, what is needed is a computational methodology for calculating atomic forces that delivers an adequate level of accuracy while consuming a reasonable amount of computing resources.

Molecular dynamics use atomic positions (and possibly charges, bonds, or other structural information) to calculate interatomic forces of each atom, which are consequently used to modify the velocities of atoms in the simulation. The resulting trajectories of the atoms are utilized to describe physical phenomena, such as, but not limited to ionic transport in batteries and fuel cells, chemical reactions during bulk and surface material degradation, and solid-state material phase change. A tradeoff exists between the accuracy and size (measured by number of atoms and simulated dynamics time) of the simulation depending on the underlying method used to calculate the atomic forces. As set forth above, one accurate but expensive method uses the ab-initio quantum mechanics approach, known as ab-initio molecular dynamics (AIMD).

FIG. 1 depicts schematic graph 100 showing the tradeoff between scale and accuracy for different prior art MD force calculation methods, e.g., AIMD 102, force field MD 104, and coarse-grained MD 106. The y-axis 108 is accuracy and the x-axis 110 is scale (e.g., 100 atoms, 1-10K atoms and 100K atoms). AIMD 102 can be utilized to model anti-stiction coating degradation. Through force field fitting 112, force field MD can be utilized to model amorphous electrolytes and proton-exchange membrane fuel cells (PEMFC) bi polar plate (BPP) oxide coatings. Coarse grained MD 106 can be utilized to model PEMFC nafion polymers.

AIMD is too computationally demanding for many relevant applications. For instance, according to one estimation, an AIMD simulation on a high-performance computer with two hundred (200) cores would take sixty-five (65) years to complete to study the dynamics behavior of amorphous lithium phosphate glass with about five hundred (500) atoms for five hundred (500) nanoseconds.

An alternative to AIMD is classical molecular dynamics. Using this alternative, interatomic forces have been fitted into some closed functional forms to enable several orders of magnitude speedup over AIMD. This alternative approach has been used to simulate large systems, such as polymers and amorphous materials. According to one estimation, the same simulation identified above using the classical molecular dynamics approach finishes in under two (2) days.

One of the drawbacks of the classical molecular dynamics model using pre-defined functional forms is that they restrict the behavior of interatomic interactions within assumptions that remain valid under certain conditions. For example, a classical force field with quadratic functional forms for the bond between atoms assumes that the chemical bond between atoms do not break. This assumption is contrary to the behavior of nature where chemical bonds in molecules form and break during chemical reactions. Relatively more complex pre-assumed functional forms for simulating chemical reactions exist. For example, reactive force fields, such as ReaxFF, is one such model. These models suffer from the disadvantage of being difficult to parametrize and require a large number of relatively complex handcrafted, closed functional forms.

As described above, NNFF algorithms exist that require the computation of quantum mechanics energies. One implementation of NNFF uses rotation-invariant features developed by Behler and Parrinello (otherwise referred to as the Behler-Parrinello approach), as described in the following articles: J. Behler and M. Parrinello, "Generalized Neural-Network Representation of High-Dimensional Potential-Energy Surfaces", Phys. Rev. Lett. 98, 146401 (2007); M. Gastegger, J. Behler, and P. Marquetand, "Machine Learning Molecular Dynamics for Simulation of Infrared Spectra", Chem. Sci. 2017, 8, 6924; and J. Behler, "Atom-centered Symmetry Functions for Constructing High-Dimensional Neural Network Potentials", J. Chem. Phys., 134, 074106 (2011), all of which are incorporated by reference in their entirety herein.

In this implementation, atoms surrounding central atom i within a predefined radius $R_c$ are used as inputs into the neural network. Instead of using atomic Cartesian coordinates of the atoms as the input features, the atomic Cartesian coordinates are converted into fingerprint feature vectors. These vectors are invariant under physical operations that should not change the energy coordinates of the local atomic structure. These physical operations include rotation, translation, and purmutation. Rotation-invariance refers to the energy invariance upon rotating the entire Cartesian coordinates of the local atomic environment by an identical rotation with respect to an arbitrary point in space, such as the central atom i. Translational-invariance refers to the energy invariance upon shifting the entire Cartesian coordinates of the local atomic environment by an identical displacement. Permutation-invariance refers to the energy invariance upon changing the ordering sequence of the atoms in the local atomic environment and keeping their positions fixed. In addition to satisfying these three (3) conditions, the chosen fingerprint feature vectors may also satisfy the following criteria (which are assumed to be consistent with the physics of the system): decaying contribution from atoms further away from the central atom i (down to 0 for $R > R_c$); and smoothly varying as the atomic positions vary smoothly in the local atomic environment.

In one implementation, these five (5) requirements are accomplished by converting a list of atomic coordinates surrounding a central atom i $\{\vec{R_i}\}$ into fingerprint feature vectors $\{\vec{G_i}\}$ described by two-body and three-body functions. Some non-limiting examples of fingerprint functions are listed below:

$$G_i^1 = \sum_j f_c(R_{ij}) \tag{1}$$

$$G_i^2 = \sum_j e^{-\eta(R_{ij}-R_s)^2} \cdot f_c(R_{ij}) \tag{2}$$

$$G_i^3 = \sum_j \cos(\kappa R_{ij}) \cdot f_c(R_{ij}) \tag{3}$$

$$G_i^4 = 2^{1-\zeta} \sum_{j,k \neq i}^{all} (1 + \lambda \cos\theta_{ijk})^\zeta \cdot e^{-\eta(R_{ij}^2 + R_{ii}^2 + R_{jk}^2)} \cdot f_c(R_{ij}) \cdot f_c(R_{ik}) \cdot f_c(R_{jk}) \tag{4}$$

-continued $$G_i^5 = 2^{1-\zeta} \sum_{j,k \neq i}^{all} (1 + \lambda\cos\theta_{ijk})^{\zeta} \cdot e^{-\eta(R_{ij}^2 + R_{ik}^2)} \cdot f_c(R_{ij}) \cdot f_c(R_{ik}) \quad (5)$$

where $\eta$, $\kappa$, $\zeta$, and $\lambda$ are user-defined parameters of G fingerprint functions as described in J. Behler, "Atom-centered Symmetry Functions for Constructing High-Dimensional Neural Network Potentials", J. Chem. Phys., 134, 074106 (2011). The values of these parameters are typically chosen to appropriately cover the length-scales relevant for the local atomic system under consideration (typically within a cutoff radius $R_c$<10 A). The cutoff function $f_c$ depends on $R_c$ and can be defined as follows:

$$f_c(R_{ij}) = \begin{cases} 0.5 \cdot \left[\cos\left(\frac{\pi R_{ij}}{R_c}\right) + 1\right] & \text{for } R_{ij} \leq R_c \\ 0 & \text{for } R_{ij} > R_c \end{cases} \quad (6)$$

The permutation-invariance is only true for atoms of the same elements. For example, exchanging a C atom at position 1 and a C atom at position 2 describes two systems with the same physics, and accordingly, the permutation-invariance holds true. As another example, exchanging a C atom at position 1 and an O atom at position 2 describes two systems with different physics, and permutation-invariance does not hold true. Consequently, when multi-element systems are investigated, the summations in the G functions above should only be done for atoms with the same elements (for two-body G's) or same element-pairs (for three-body G's). Given m number of elements in a MD system of interest surrounding a central atom i, m different G's are calculated for each parameterized 2-body function and m(m+1)/2 different G's for each parametrized three-body function. Due to the construction of these functions (including rotational invariance), these functions provide beneficial representations for learning the rotation-invariant nature of quantum mechanics. However, a machine learning system using these invariant features are limited to use to predict rotation-invariant outputs such as energy.

Figure 2:
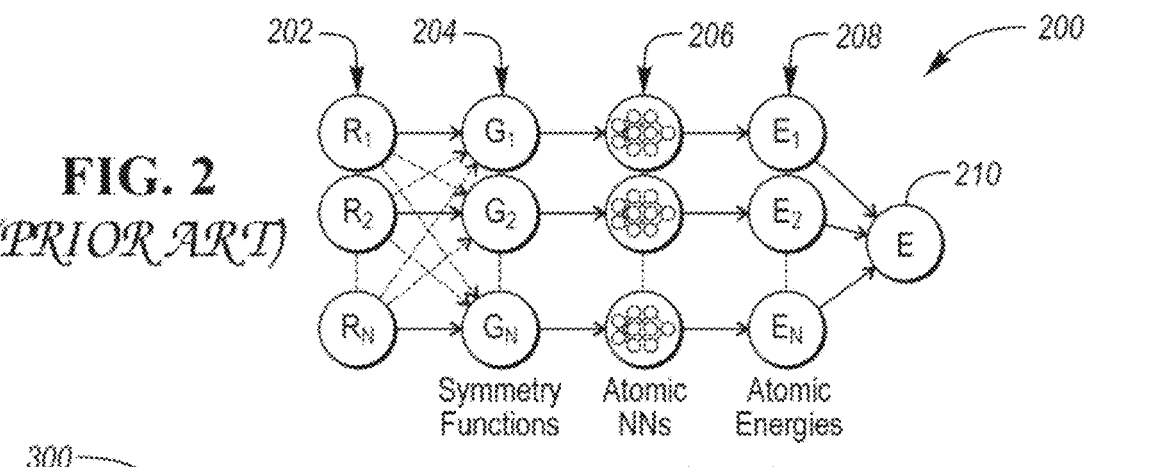
FIG. 2 is a neural network node schematic diagram of a neural network force field (NNFF) energy prediction scheme under the prior art Behler-Parrinello approach.

Many methodologies based on quantum mechanics (e.g., density functional-theory) are used to calculate energy E of a system. However, these methodologies cannot conveniently partition the electronic energy into contributions from individual atoms. Accordingly, in one or more embodiments, $\{\vec{t}_i\}$ feature vectors for each atom in a system are calculated and then utilized to train or predict a single scalar quantity of energy E as shown in FIG. 2. FIG. 2 depicts a neural network node schematic diagram of an NNFF energy prediction scheme under the prior art Behler-Parrinello approach. Atomic coordinate environments $R_1$ through $R_N$ 202 are used as inputs, respectively, of NNFF algorithm 200. Atomic coordinate environments $R_1$ through $R_N$ 202 are used to calculate symmetry functions $G_1$ through $G_N$ 204. Each atomic coordinate environment $R_1$ through $R_N$ 202 are interrelated with each symmetry function $G_1$ through $G_N$ 204. Atomic NNs 206 are trained using symmetry functions $G_1$ through $G_N$ 204 to obtain atomic energies 208, which are used to obtain total energy E 210.

The NNFF approach for AIMD applications suffers from one or more limitations. For instance, during a training cycle, each of the atomic NNs (typically one NN for each element) is co-trained to a single energy quantity E, which is tied to the system of interest. Accordingly, the NNs are co-dependent because each needs to be co-used to predict a single energy value E and are only optimized for predicting the exact MD system used in the training set. There are no independent $\{\vec{R}_i\} \rightarrow E_i$ samples that can be included for the training of different MD systems containing local atomic environments similar to $\{\vec{R}_i\}$. Secondly, during MD runtime (force prediction cycle), expensive calculations are performed to calculate the force vector $\vec{F}_i$ on atom i. $\vec{F}_i$ is the derivative of total system energy E with respect to displacement of a single atom $\vec{R}_i$. However, prediction of E requires knowing G for all atoms in the MD system $\{\vec{G}_1, \vec{G}_2, \ldots, \vec{G}_N\}$. Consequently, calculating $\vec{F}_i$ requires calculating the fingerprint vector 3N times, as shown in the equation below.

$$F_{k,\alpha} = -\frac{\partial E}{\partial R_{k,\alpha}} = -\sum_{i=1}^{N} \frac{\partial E_i}{\partial R_{k,\alpha}} \quad (7)$$

$$= -\sum_{i=1}^{N} \sum_{j=1}^{M_i} \frac{\partial E_i}{\partial G_{i,j}} \frac{\partial G_{i,j}}{\partial R_{k,\alpha}}$$

where $\alpha$ indicates the Cartesian x, y, and z axes, N is the total number of atoms in the MD system, and $M_i$ is the total number of fingerprint functions describing atom i. Accordingly, calculating forces for all N atoms in the system grows with $O(N^2)$. In certain implementations, certain algorithm modifications can reduce the number of fingerprint vector calculations to 3P times, where P is the average number of atoms in the local atomic environment of the atoms, reducing the computational cost scale to O(N). Nevertheless, this restriction requires 3P $\{\vec{G}_i\}$ calculations for one $\vec{F}_i$ prediction (P may range from 100 to 400 atoms depending on the chosen $R_c$), as opposed to one $\{\vec{G}_i\}$ calculation in a direct $\vec{F}_i$ prediction. Accordingly, an NNFF algorithm with direct $\vec{F}_i$ prediction can accelerate NNFF-based MD $\vec{F}_i$ calculations by two (2) to three (3) orders of magnitude.

In one or more embodiments, a computer system configured to implement an algorithm to directly predict quantum mechanics atomic forces from a molecular structure using a neural network without using energy derivatives is disclosed. In certain embodiments, this algorithm may be two (2) to (3) orders of magnitude less computationally demanding (e.g., less computing time of a high-performance computing (HPC) system) compared to known NNFF algorithms requiring the computation of quantum mechanics energies.

The ability of an HPC system to perform certain tasks can be quantified using benchmarks, such as application benchmarks from computational codes, such as those represented in the Standard Performance Evaluation Corporation's SPEC HPC2002 and SPEC MPI2007 suites (www.spec.org/hpg) and in the US National Science Foundation (NSF) HPC system acquisitions process, which are hereby incorporated by reference in their entirety.

In one or more embodiments, simpler functional forms of classical molecular dynamics models are replaced with neural networks. Such networks can be easily tuned according to a supplied [input, output] dataset. Local environment of atoms surrounding an atom i can be used to predict the force experienced by atom i. In a usual NNFF model, center atom i is displaced and then the change in energy contribution from atom i and all other atoms near i are calculated. The numerical derivative of total system energy versus atom i displacement is the atomic force experienced by atom i. This approach is time consuming because the change of energy contribution from all the atoms surrounding atom i need to be calculated to calculate force. In one or more embodiments, systems disclosed herein directly predict the force on atom i. This computational system may be two (2) to three (3) magnitudes faster than the entire system approach because there is no need to calculate additional contribution from other atoms surrounding atom i, while maintaining the requisite accuracy.

In one embodiment, a computational algorithm is disclosed that is configured to directly predict a force vector on an atom by analyzing the local atomic environment surrounding a center atom. A neural network may be trained on rotationally-invariant features of a local atomic environment. The trained neural network is configured to predict the atomic forces within a MD simulation. In one or more embodiments, rotationally-invariant features may be adapted to predict a relatively small number of rotation-invariant intermediate states. Subsequently, a number of rotationally covariant features can be added to these rotationally invariant intermediate states, which then can be used on a later part of the neural network to predict force vector values. The force vector values represent rotationally covariant output.

In one embodiment, because this computational algorithm enables a direct $\{\vec{R}_\iota\} \rightarrow \vec{F}_\iota$ prediction for each training sample (unlike E prediction which requires knowing all $\{\vec{R}_\iota\}$ data samples in the simulation frame), $\{\vec{R}_\iota\} \rightarrow \vec{F}_\iota$ samples from different sets of systems or materials can be combined for the force field training and/or development. For instance, the computational algorithm of one or more embodiments can be used to develop a force field for a large atomic system of the interface between materials A and B. Using this algorithm, a training set can be created by combining separate smaller structures of material A, material B, and the interface between materials A and B. This training set cannot be created using an algorithm which requires E prediction as part of the routine because the E of the combined large atomistic system is too expensive to calculate from quantum mechanics from a computational standpoint.

The computational algorithm of one or more embodiments may be integrated into an MD simulation engine to perform an MD simulation with accuracy close to that of a significantly more expensive AIMD method. For example, the MD simulation of one or more embodiments may be useful for modeling atom/ion dynamics and chemical reactions relevant for functional materials used in fuel cells, water desalination, catalysis, coatings, and batteries.

In one or more embodiments, the atomic force prediction algorithm of one or more embodiments is integrated into MD software. A non-limiting example of suitable MD software is Large-scale Atomic/Molecular Massively Parallel Simulator (LAMMPS). LAMMPS is available from Sandia National Laboratories, located in Albuquerque, N. Mex. LAMMPS uses a Message Passing Interface (MPI) for parallel communication. LAMMPS is open-source software, distributed under the terms of the GNU General Public License.

A main principle of this algorithm to enable direct force prediction is a definition of a set of k internal axes $\{\vec{A}_\iota\} = \{\vec{A}_{\iota,1}, \vec{A}_{\iota,2}, \ldots, \vec{A}_{\iota,k}\}$ for each atomic coordinate environment $\{\vec{R}_\iota\}$ which rotates with the local atomic environment structure (rotationally-covariant vectors), then projects the rotationally-covariant force vector $\vec{F}_\iota$ onto $\{\vec{A}_\iota\}$ to obtain the internal force vector $\vec{F}_{int,i}$. Because $\vec{F}_{int,i}$ is later projected back to the Cartesian coordinate, k is a fixed number and is larger than or equal to 3. Even though both $\{\vec{A}_\iota\}$ and $\vec{F}_\iota$ are rotationally-covariant, these vectors are rigid vectors with respect to the local atomic structure itself (both vectors rotate with the structure). Accordingly, a rotation transformation $\hat{T} \in SO(3)$ of the atomic positions $\{\vec{R}_\iota\} \rightarrow \hat{T}\{\vec{R}_\iota\}$ correspondingly rotates $\vec{F}_\iota \rightarrow \hat{T}\vec{F}_\iota$ and $\{\vec{A}_\iota\} \rightarrow \hat{T}\{\vec{A}_\iota\}$. Consequently, the internal projection vector $\vec{F}_{int,i}$ is rotationally-invariant. In one or more embodiments, the rotationally-invariant feature vector $\{\vec{G}_\iota\}$ is used to predict the rotationally-invariant intermediate state $\vec{F}_{int,i}$. The rotationally-invariant $\vec{F}_{int,i}$ and the rotationally-covariant $\{\vec{A}_\iota\}$ are used to perform an inverse projection and obtain the rotationally-covariant output Cartesian central atom force $\vec{F}_\iota$. A summary of invariant and covariant vector notations is shown in Table 1 below.

TABLE 1

| Description | Vector | Under rotation $\hat{T} \in SO(3)$ |
| --- | --- | --- |
| Cartesian position of atomic environment surrounding atom i (out of N) | $\{\vec{R}_\iota\}$ | $\hat{T}\{\vec{R}_\iota\}$ |
| Internal axis number k (out of at least 3) | $\{\vec{A}_\iota\}$ | $\hat{T}\{\vec{A}_\iota\}$ |
| Cartesian force of atom i (out of N) | $\vec{F}_\iota$ | $\hat{T}\vec{F}_\iota$ |
| Projection of force of atom i (out of N) on internal axis number k (out of at least 3) | $F_{int,i,k} = \vec{F}_{int,i} \cdot \vec{A}_{\iota,k}$ | Unchanged |
| List of fingerprints centered at atom i | $\{\vec{G}_\iota\}$ | Unchanged |

A set of internal axes $\{\vec{A}_\iota\} = \{\vec{A}_{\iota,1}, \vec{A}_{\iota,2}, \ldots, \vec{A}_{\iota,k}\}$ is defined, where k indicates a group of at least some of the atoms surrounding the central atom i. The criteria for whether an atom j is considered as part of group k or not is user-defined and can be further optimized depending on the MD system under consideration. Once this atom grouping criteria has been determined, the constraint that $\vec{A}_{\iota,k}$ should be the weighted average of all the relative position vectors of atoms in the group relative to the central atom i is applied. This constraint can be written mathematically as:

$$\vec{V}_{i,k} = \sum_{j \in k} f_{A,k}(R_{ij}) \cdot \vec{R}_{ij} \cdot f_c(R_{ij}) \quad (8)$$

$$\vec{A}_{i,k} = \begin{cases} 0 & \text{for } \vec{V}_{i,k} = 0 \\ \vec{V}_{i,k} / |\vec{V}_{i,k}| & \text{otherwise} \end{cases} \quad (9)$$

$$f_c(R_{ij}) = \begin{cases} 0.5 \cdot \left[ \cos\left(\frac{\pi R_{ij}}{R_c}\right) + 1 \right] & \text{for } R_{ij} \leq R_c \\ 0 & \text{for } R_{ij} > R_c \end{cases} \quad (10)$$

where $f_{A,k}$ is an axis function as described herein. In one or more embodiments, the same $R_c$ for the $\vec{A}_{i,k}$ calculation as the one for $\{\vec{G}_i\}$ calculation is set. In other embodiments, more stable $\vec{A}_{i,k}$ vectors with respect to variation in local atomic coordinates are set because $\vec{A}_{i,k}$ are only used for vector projection reference axes. The following $g_A$ parametrized functional forms are used in place of $f_{A,k}$ for the polyethylene oxide (PEO) polymer $(C_2H_4O)_n$:

$$g_A^1(R_{ij}) = e^{-\eta R_{ij}^2}, \eta = 1.0 \quad (11)$$

$$g_A^2(R_{ij}) = e^{-\eta(R_{ij}-R_s)^2}, \eta = 2.0, R_s = 1.0$$

In the example of an NNFF development for PEO, the grouping criteria is outlined below in Table 2:

TABLE 2

| k | Criteria for atom j inclusion in group k | Parametrized function for $f_{A,k}$ |
|---|---|---|
| 1 | j is of atomic element C | $g_A^1$ |
| 2 | j is of atomic element H | $g_A^1$ |
| 3 | j is of atomic element O | $g_A^1$ |
| 4 | j is of atomic element C | $g_A^2$ |
| 5 | j is of atomic element H | $g_A^2$ |
| 6 | j is of atomic element O | $g_A^2$ |

Once the way to calculate $\{\vec{A}_i\}$ from $\{\vec{R}_i\}$ is defined, $\vec{F}_i$ is projected (using quantum mechanics) onto $\{\vec{i}\}$ to find a set of internal force projection $\vec{F}_{int,i}$. Since both $\{\vec{G}_i\}$ and $\vec{F}_{int,i}$ are rotationally-invariant, a first neural network (NN1) can be trained to directly perform the $\{\vec{G}_i\} \to \vec{F}_{int,i}$ prediction. As the next step, an inverse projection from the internal force $\vec{F}_{int,i}$ back to the Cartesian atomic force $\vec{F}_i$ is performed. In one embodiment, because the relationship $\vec{F}_{int,i} = \{\vec{A}_i\}\vec{F}_i$ holds, the inverse projection is performed using a matrix pseudo-inverse relationship to find the least-square-error solution: $\vec{F}_i = (\{\vec{A}_i\}^T\{\vec{A}_i\})^{-1}\{\vec{A}_i\}\vec{F}_{int,i}$. In practice, this may not give suitable results because the set of internal axes $\{\vec{A}_i\}$ may not be constrained to be an orthogonal (or close-to-orthogonal) basis for the entire 3D-xyz space. Accordingly, if the basis vectors overlap, small amounts of noise (whether from error or from perturbations of atomic coordinates) can lead to numerical instabilities. While this is not an issue if there is zero error in the $\vec{F}_{int,i}$ prediction, any error in $\vec{F}_{int,i}$ prediction by NN1 can be amplified by several orders of magnitude by the pseudo-inverse method during $\vec{F}_i$ calculation. This makes matrix least-squares or pseudo-inversion method unsuitable for doing inverse projection of the force vector in one or more embodiments.

A second, smaller neural network (NN2) may be trained to address the inverse projection problem. $\vec{F}_{int,i}$ and $\{\vec{i}\}$ are used as the inputs to NN2 and NN2 predicts $\vec{F}_i$ as the output. In one or more embodiments, NN2 takes some degree of rotational symmetry into account by performing data augmentation. In one or more embodiments, not only $(\vec{F}_{int,i}, \{\vec{A}_i\}) \to \vec{F}_i$ but also $(\vec{F}_{int,i}, \hat{T}\{\vec{A}_i\}) \to \hat{T}\vec{F}_i$ are used as part of the training samples, where $\hat{T}$ is a random 3D rotation matrix (many different $\hat{T}$'s can be used for NN2 data augmentation).

As the next step, NN1 and NN2 may be combined into a single neural network by transferring the weights and biases of NN1 and NN2 into a combined NN architecture with node dimensions identical to NN1 and NN2 (transfer learning). Error of the combined NN may be reduced and/or minimized by running a smaller number of training cycles on the combined network using the $(\{\vec{G}_i\}, \{\vec{A}_i\}) \to \vec{F}_i$ training dataset.

Figure 3:
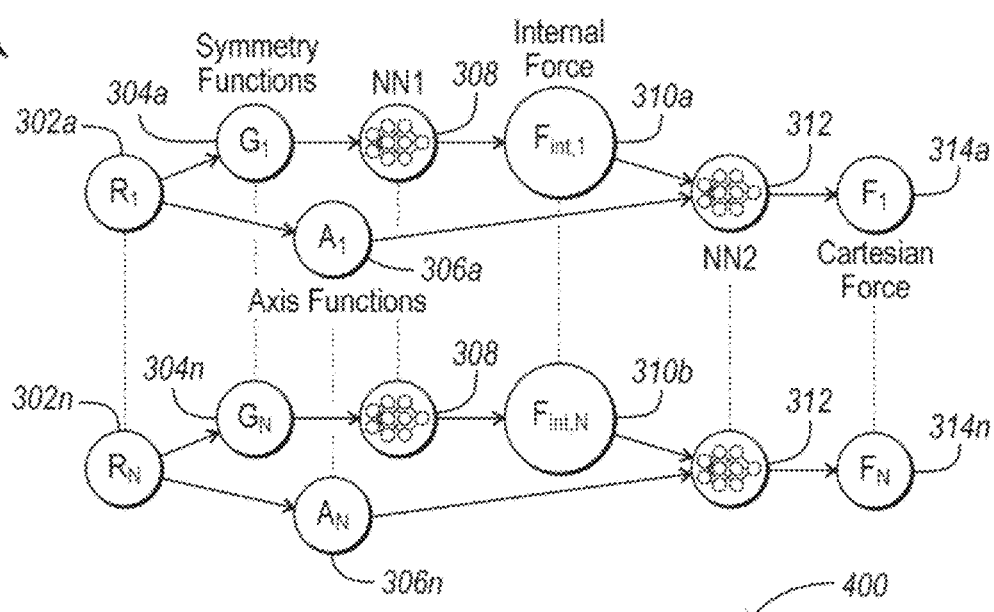
FIG. 3 depicts a neural network node schematic of an NNFF algorithm according to one embodiment.

The modifications to an NNFF algorithm identified above in one or more embodiments enable force prediction simplification, where rotationally-invariant and rotationally-covariant features are used to enable direct prediction of atomic force on atom i $(\vec{F}_i)$ given just the local atomic environment $\{\vec{R}_i\}$ coordinates and elements surrounding atom i. FIG. 3 depicts a neural network node schematic of an NNFF algorithm 300 according to one embodiment. Atomic coordinate environments $R_1$ through $R_N$ are used as inputs 302a through 302n, respectively, of NNFF algorithm 300. Atomic coordinate environments $R_1$ through $R_N$ are used to calculate symmetry functions $G_1$ through $G_N$ (referred to as symmetry functions 304a through 304n of FIG. 3) and axis functions $A_1$ through $A_N$ (referred to as symmetry functions 306a through 306n of FIG. 3). First neural network NN1 (referred to as 308 on FIG. 3) is trained using symmetry functions $G_1$ through $G_N$ to obtain internal force vectors $F_{int,1}$ through $F_{int,N}$ (referred to as 310a through 310n of FIG. 3). Axis functions $A_1$ through $A_N$ and internal force vectors $F_{int,1}$ through $F_{int,N}$ are used to train second neural network NN2 (referred to as 312 of FIG. 3). The output of NNFF algorithm 300 is atomic forces $F_1$ through $F_N$ (referred to as 314a through 314n of FIG. 3) in the cartesian coordinate system. In one or more embodiments, the NNFF algorithm 300 of FIG. 3 has no interdependence between the $\{\vec{R}_i\}$ training data samples. Accordingly, direct $\{\vec{i}\} \to \vec{F}_i$ prediction can be performed, which significantly improves computational speed of force prediction.

In one example, a bulk version of polyethylene oxide (PEO) polymer, as shown below, is used to generate a training set of H atoms of PEO using fingerprint $\{\vec{G}_i\}$ for $\vec{F}_i$ prediction.

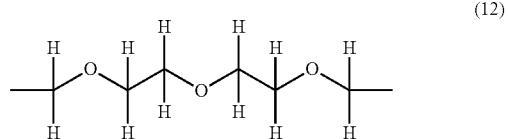

(12)

Figure 4:
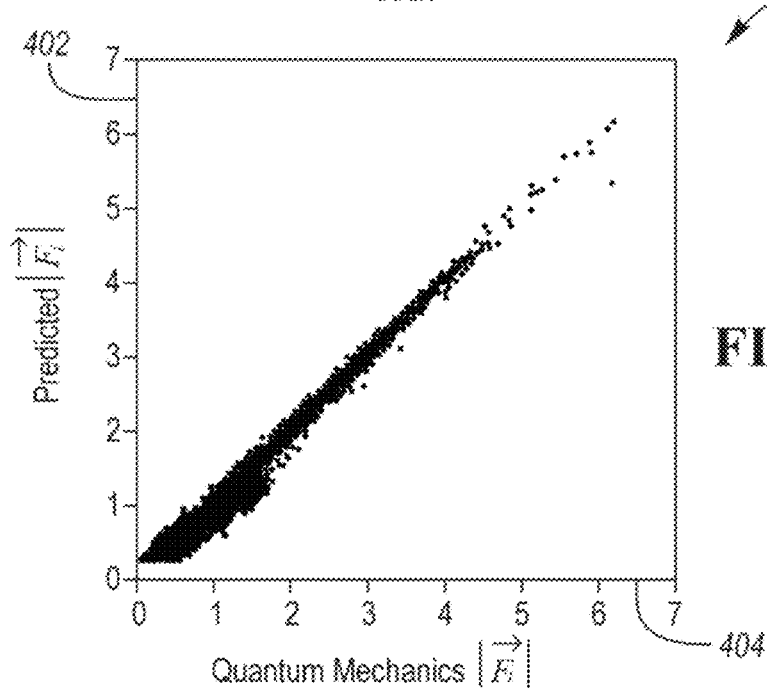
FIG. 4 is a graph of predicted force using an NNFF algorithm of one embodiment versus quantum mechanics calculated force for bulk polyethylene oxide (PEO).

FIG. 4 is a graph 400 of $|\vec{F}_i|$ 402 predicted using an NNFF algorithm of one embodiment versus $|\vec{F}_i|$ 404 calculated using a quantum mechanics density functional theory (DFT) simulation. Graph 400 shows the forces on the H atoms for PEO using the two different approaches. The error between the NNFF algorithm and the quantum mechanics DFT simulation can be expressed as Error=$(|\vec{F}_{i,NN}|-|\vec{F}_{i,QM}|)^2$. Using this expression, the average error is 0.01 $(eV/A)^2$, which is within an acceptable range. In this example, no samples from the test set were seen during the training cycle.

FIG. 5A shows diagram 500 of fingerprint neural network (NN) 502 of an NNFF algorithm of one embodiment. Rotation-invariant component 504 of the fingerprint NN corresponds to prediction of the internal force projection intermediate-state $\vec{F}_{int,i}$ 506. FIGS. 5B, 5C, and 5D depict graphs 508, 510 and 512, respectively, showing results for the prediction of H, C, and O atoms, respectively, in the test set of atomic snapshots taken from bulk PEO using the NNFF algorithm of one embodiment. Using the error equation set forth above, the error between the NNFF algorithm and the quantum mechanics DFT simulation is 0.01 (eV/A)$^2$, 0.04 (eV/A)$^2$, and 0.16 (eV/A)$^2$ for the prediction of H, C, and O atoms, respectively, which is within an acceptable range. In these examples, no samples from the test set were seen during the training cycle.

Figure 6A:
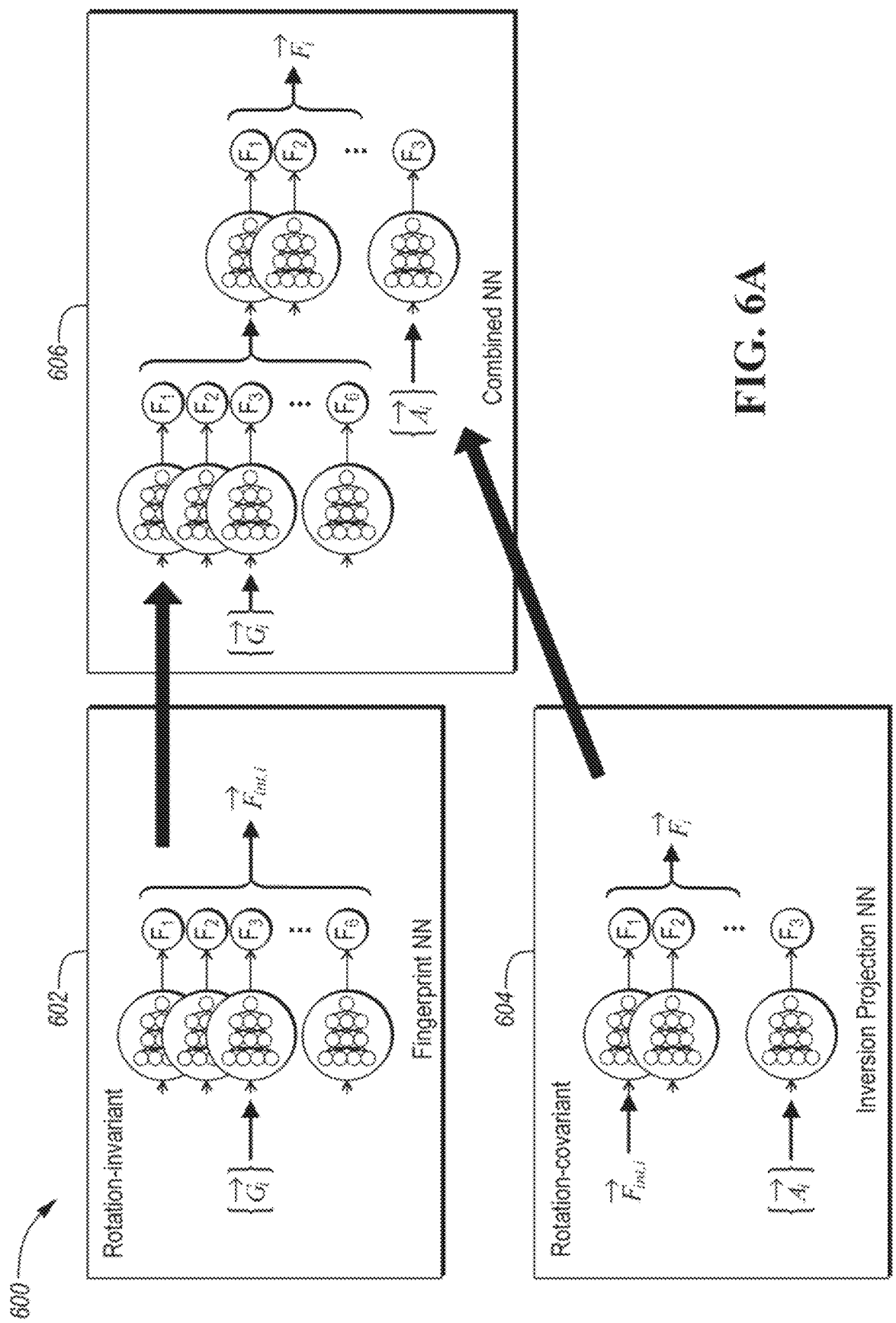
FIG. 6A shows a diagram of a fingerprint NN and an inversion projection NN combined to produce a combined NN in an NNFF algorithm of one embodiment.
Figure 6D:
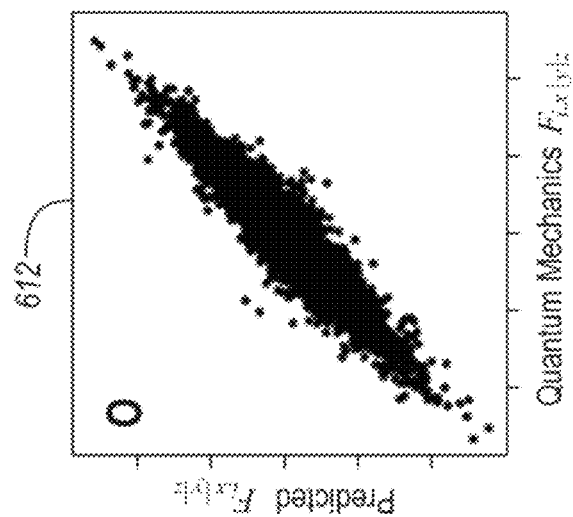
FIGS. 6B, 6C, and 6D depict graphs showing results for the predictions of H, C, and O atoms, respectively, of bulk PEO using the combined NNFF algorithm of one embodiment.
Figure 6C:
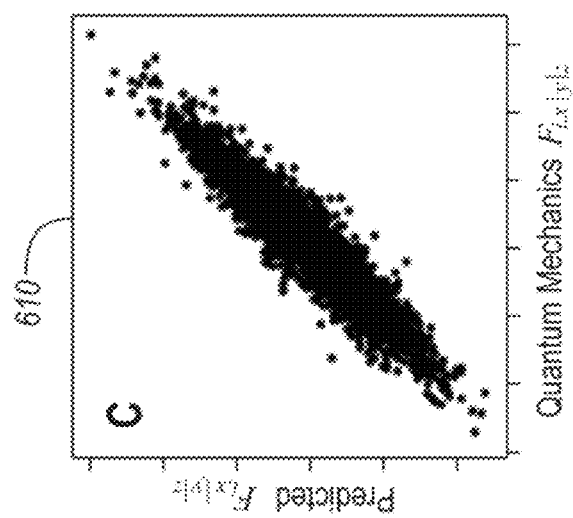
Figure 6B:
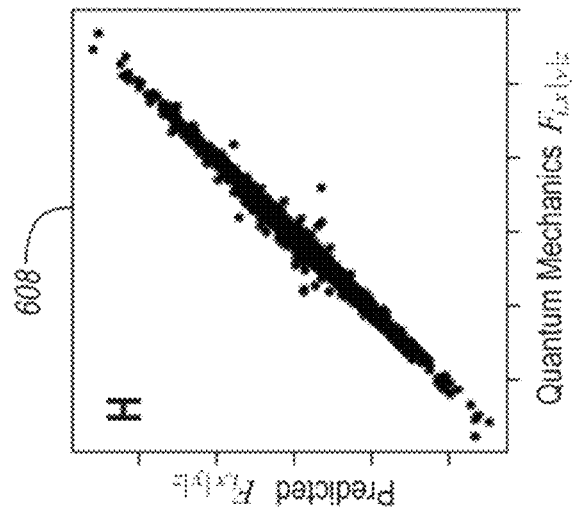

FIG. 6A shows diagram 600 of fingerprint NN 602 and inversion projection NN 604 combined to produce combined NN 606 in an NNFF algorithm of one embodiment. According to one or more embodiments, weights of NNs 602 and 604 are transferred and the combined NN 606 is retrained. Fingerprint NN 602 is a rotationally-invariant component of the NNFF algorithm and inversion projection NN 604 is a rotationally-covariant component of the NNFF algorithm. Combined NN 606 predicts Cartesian atomic force $\vec{F}_i$. FIGS. 6B, 6C, and 6D depict graphs 608, 610 and 612, respectively, showing results for the predictions of H, C, and O atoms, respectively, in the test set of atomic snapshots taken from bulk PEO using the NNFF algorithm of one embodiment. $\vec{F}_{i,x|y|z}$ denotes projection of $\vec{F}_i$ onto the Cartesian x, y, and z axis. Using the error equation set forth above, the error between the NNFF algorithm and the quantum mechanics DFT simulation is 0.03 (eV/A)$^2$, 0.58 (eV/A)$^2$, and 0.42 (eV/A)$^2$ for the prediction of H, C, and O atoms, respectively, which is within an acceptable range. In these examples, no samples from the test set were seen during the training cycle.

Figure 7:
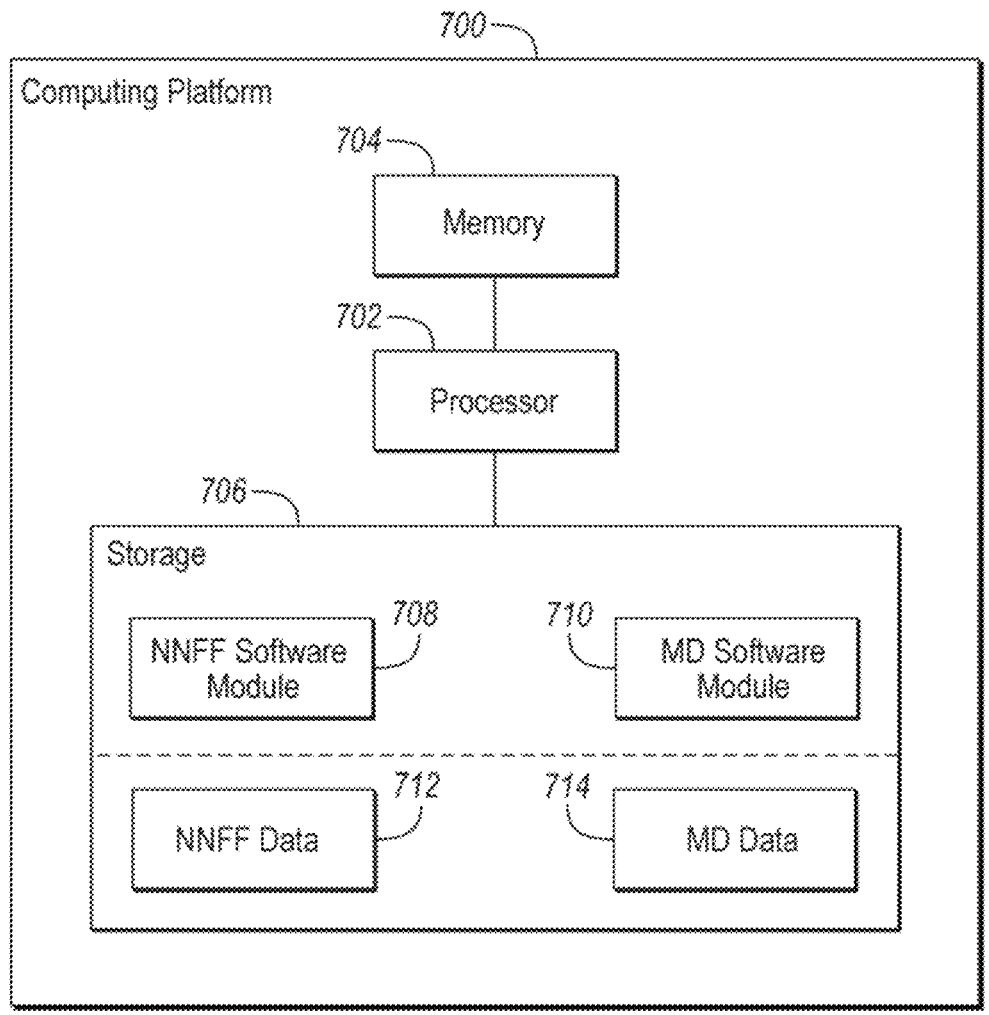

The NNFF algorithms and/or methodologies of one or more embodiments are implemented using a computing platform, such as the computing platform 700 illustrated in FIG. 7. The computing platform 700 may include a processor 702, memory 704, and non-volatile storage 706. The processor 702 may include one or more devices selected from high-performance computing (HPC) systems including high-performance cores, microprocessors, micro-controllers, digital signal processors, microcomputers, central processing units, field programmable gate arrays, programmable logic devices, state machines, logic circuits, analog circuits, digital circuits, or any other devices that manipulate signals (analog or digital) based on computer-executable instructions residing in memory 704. The memory 704 may include a single memory device or a number of memory devices including, but not limited to, random access memory (RAM), volatile memory, non-volatile memory, static random access memory (SRAM), dynamic random access memory (DRAM), flash memory, cache memory, or any other device capable of storing information. The non-volatile storage 706 may include one or more persistent data storage devices such as a hard drive, optical drive, tape drive, non-volatile solid state device, cloud storage or any other device capable of persistently storing information.

The processor 702 may be configured to read into memory 704 and execute computer-executable instructions residing in NNFF software module 708 of the non-volatile storage 706 and embodying NNFF algorithms and/or methodologies of one or more embodiments. The processor 702 may be further configured to read into memory 704 and execute computer-executable instructions residing in MD software module 710 (such as LAMMPS) of the non-volatile storage 706 and embodying MD algorithms and/or methodologies. The software modules 708 and 710 may include operating systems and applications. The software modules 708 and 710 may be compiled or interpreted from computer programs created using a variety of programming languages and/or technologies, including, without limitation, and either alone or in combination, Java, C, C++, C#, Objective C, Fortran, Pascal, Java Script, Python, Perl, and PL/SQL.

Upon execution by the processor 702, the computer-executable instructions of the NNFF software module 708 and the MD software module 710 may cause the computing platform 700 to implement one or more of the NNFF algorithms and/or methodologies and MD algorithms and/or methodologies, respectively, disclosed herein. The non-volatile storage 706 may also include NNFF data 712 and MD data 714 supporting the functions, features, and processes of the one or more embodiments described herein.

The program code embodying the algorithms and/or methodologies described herein is capable of being individually or collectively distributed as a program product in a variety of different forms. The program code may be distributed using a computer readable storage medium having computer readable program instructions thereon for causing a processor to carry out aspects of one or more embodiments. Computer readable storage media may include volatile and non-volatile, and removable and non-removable tangible media implemented in any method or technology for storage of information, such as computer-readable instructions, data structures, program modules, or other data. Computer readable storage media may further include RAM, ROM, erasable programmable read-only memory (EPROM), electrically erasable programmable read-only memory (EEPROM), flash memory or other solid state memory technology, portable compact disc read-only memory (CD-ROM), or other optical storage, magnetic cassettes, magnetic tape, magnetic disk storage or other magnetic storage devices, or any other medium that can be used to store the desired information and which can be read by a computer. Computer readable program instructions may be downloaded to a computer, another type of programmable data processing apparatus, or another device from a computer readable storage medium or to an external computer or external storage device via a network.

Computer readable program instructions stored in a computer readable medium may be used to direct a computer, other types of programmable data processing apparatus, or other devices to function in a particular manner, such that the instructions stored in the computer readable medium produce an article of manufacture including instructions that implement the functions, acts, and/or operations specified in the flowcharts or diagrams. In certain alternative embodiments, the functions, acts, and/or operations specified in the flowcharts and diagrams may be re-ordered, processed serially, and/or processed concurrently consistent with one or more embodiments. Moreover, any of the flowcharts and/or diagrams may include more or fewer nodes or blocks than those illustrated consistent with one or more embodiments.

While all of the invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of the general inventive concept.

What is claimed is:

1. A computational method for simulating the motion of elements within a multi-element system using a neural network force field (NNFF), the method comprising:
   receiving a combination of a number of rotationally-invariant features and a number of rotationally-covariant features of a local environment of the multi-element system;
   predicting a force vector for each element within the multi-element system based on the combination of the number of rotationally-invariant features and the number of rotationally-covariant features, and the NNFF, to obtain a simulated motion of the elements within the multi-element system; and
   training a first neural network (NN1) based on the number of rotationally-invariant features to predict a number of rotationally-invariant intermediate states.

2. The computational method of claim 1, further comprising training a second neural network (NN2) based on the number of rotationally-invariant intermediate states and the number of rotationally-covariant features to predict a number of rotationally-covariant outputs.

3. The computational method of claim 2, further comprising concentrating NN1 and NN2 into a third neural network (NN3) used to obtain the simulated motion of the elements within the multi-element system.

4. The computational method of claim 3, wherein the multi-element system is a material system, the elements are atoms within the material system, and the local environment is an atomic local environment.

5. The computational method of claim 4, wherein the number of rotationally-covariant features include a set of internal axes $\{\vec{A}_{i,j}\}$.

6. The computational method of claim 5, wherein the number of rotationally-invariant intermediate states includes a scalar projection of an atomic force experienced by a center atom i ($\vec{F}_i$) to the set of internal axes $\{\vec{A}_{i,j}\}$.

7. The computational method of claim 6, wherein the number of rotationally-covariant output includes a set of Cartesian components of the atomic force experiences by the center atom i ($\vec{F}_i$).

8. The computational method of claim 1, wherein the number of rotationally-invariant features include one or more Behler-Parrinello type fingerprint feature vectors.

9. The computational method of claim 1, wherein the multi-element system is a portion of: a fuel cell, a water desalination system, a catalysis system, a coating system, or a battery.

10. A non-transitory computer-readable medium tangibly embodying computer readable instructions for a software program, the software program being executable by a processor of a computing device to provide operations comprising:
    receiving a combination of a number of rotationally-invariant features and a number of rotationally-covariant features of a local environment of a multi-element system having elements;
    predicting a force vector for each element within the multi-element system based on the combination of the number of rotationally-invariant features and the number of rotationally-covariant features, and a neural network force field (NNFF), to obtain a simulated motion of the elements within the multi-element system; and
    training a first neural network (NN1) based on the number of rotationally-invariant features to predict a number of rotationally-invariant intermediate states.

11. The non-transitory computer-readable medium of claim 10, wherein the software program is executable by the processor of the computing device to provide the further operation of training a second neural network (NN2) based on the number of rotationally-invariant intermediate states and the number of rotationally-covariant features to predict a number of rotationally-covariant outputs.

12. The non-transitory computer-readable medium of claim 11, wherein the software program is executable by the processor of the computing device to provide the further operation of concentrating NN1 and NN2 into a third neural network (NN3) used to obtain the simulated motion of the elements within the multi-element system.

13. The non-transitory computer-readable medium of claim 10, wherein the number of rotationally-invariant features include one or more Behler-Parrinello type fingerprint feature vectors.

14. A computer system for simulating the motion of elements within a multi-element system using a neural network force field (NNFF) including a simulation computer having a processor for executing computer-readable instructions and a memory for maintaining the computer-executable instructions, the computer-executable instructions when executed by the processor perform the following functions:
    receiving a combination of a number of rotationally-invariant features and a number of rotationally-covariant features of a local environment of the multi-element system having elements;
    predicting a force vector for each element within the multi-element system based on the combination of the number of rotationally-invariant features and the number of rotationally-covariant features, and the NNFF, to obtain a simulated motion of the elements within the multi-element system; and
    training a first neural network (NN1) based on the number of rotationally-invariant features to predict a number of rotationally-invariant intermediate states.

15. The computer system of claim 14, wherein the computer-executable instructions when executed by the processor performs the further function of training a second neural network (NN2) based on the number of rotationally-invariant intermediate states and the number of rotationally-covariant features to predict a number of rotationally-covariant outputs.

16. The computer system of claim 15, wherein the computer-executable instructions when executed by the processor performs the further function of concentrating NN1 and NN2 into a third neural network (NN3) used to obtain the simulated motion of the elements within the multi-element system.

17. The computer system of claim 16, wherein the multi-element system is a material system, the elements are atoms within the material system, and the local environment is an atomic local environment.

18. The computational method of claim 17, wherein the number of rotationally-covariant features include a set of internal axes $\{\vec{A}_{i,j}\}$.

19. The computational method of claim 18, wherein the number of rotationally-invariant intermediate states includes a scalar projection of an atomic force experienced by a center atom i ($\vec{F_i}$) to the set of internal axes $\{\vec{A_i}\}$.

20. The computer system of claim 14, wherein the number of rotationally-invariant features include one or more Behler-Parrinello type fingerprint feature vectors.

* * * * *